(12) United States Patent
Winqvist et al.

(10) Patent No.: US 8,187,245 B2
(45) Date of Patent: May 29, 2012

(54) ABSORBENT ARTICLE, BELT STRUCTURE, MANUFACTURING METHOD FOR A BELT STRUCTURE AND MANUFACTURING METHOD FOR AN ABSORBENT ARTICLE

(75) Inventors: Pontus Winqvist, Stora Höga (SE); Kent Hermansson, Västra Frölunda (SE)

(73) Assignee: SCA Hygiene Products AB, Göteborg (SE)

( * ) Notice: Subject to any disclaimer, the term of this patent is extended or adjusted under 35 U.S.C. 154(b) by 396 days.

(21) Appl. No.: 12/442,849

(22) PCT Filed: Sep. 28, 2006

(86) PCT No.: PCT/EP2006/009443
§ 371 (c)(1),
(2), (4) Date: Mar. 25, 2009

(87) PCT Pub. No.: WO2008/037283
PCT Pub. Date: Apr. 3, 2008

(65) Prior Publication Data
US 2010/0010465 A1   Jan. 14, 2010

(51) Int. Cl.
*A61F 13/15* (2006.01)
(52) U.S. Cl. .................. 604/389; 604/387; 604/385.03
(58) Field of Classification Search ............ 604/385.01, 604/385.03, 385.11, 385.16, 386–392
See application file for complete search history.

(56) References Cited

U.S. PATENT DOCUMENTS

| | | | | |
|---|---|---|---|---|
| 6,494,873 B2 * | 12/2002 | Karlsson et al. | ............... | 604/392 |
| 6,726,670 B2 | 4/2004 | Almberg et al. | | |
| 7,347,848 B2 * | 3/2008 | Fernfors | ........................ | 604/392 |
| 7,867,213 B2 * | 1/2011 | Bandorf et al. | ................ | 604/394 |
| 2002/0045881 A1 | 4/2002 | Kusibojoska et al. | | |
| 2002/0058923 A1 | 5/2002 | Surprise et al. | | |
| 2002/0091369 A1 * | 7/2002 | Hansson | ........................ | 604/392 |
| 2002/0193776 A1 | 12/2002 | Fernfors | | |
| 2003/0050616 A1 * | 3/2003 | Reynolds et al. | ............. | 604/369 |
| 2006/0167433 A1 * | 7/2006 | D'Alcini | ........................ | 604/392 |
| 2007/0049897 A1 * | 3/2007 | LaVon et al. | ................... | 604/392 |

(Continued)

FOREIGN PATENT DOCUMENTS

DE     197 32 499 A1    2/1999

(Continued)

OTHER PUBLICATIONS

Decision on Grant Patent for Invention dated Jul. 30, 2010, issued in the corresponding Russian Application No. 2009115863, and an English Translation thereof.

Form PCT/ISA/210 (International Search Report) dated Jun. 22, 2007.

(Continued)

*Primary Examiner* — Michele M Kidwell
(74) *Attorney, Agent, or Firm* — Buchanan Ingersoll & Rooney PC

(57) ABSTRACT

The disclosure relates to an absorbent article including a top-sheet having an inner side and an outside and a back-sheet having an inner side and an outside and the inner side of the back-sheet being directed towards the inner side of the top-sheet. At least one elongate belt is provided which has a free end portion for fastening the absorbent article around the waist of a wearer and an attachment end portion that is fixedly attached to the outside of the back-sheet or to the outside of the top-sheet, whereas the free end portion is arranged within the boundaries of the top-sheet and/or the back-sheet.

13 Claims, 9 Drawing Sheets

U.S. PATENT DOCUMENTS

2007/0066952 A1\* 3/2007 LaVon et al. .................. 604/392
2007/0066954 A1\* 3/2007 LaVon et al. .................. 604/392

FOREIGN PATENT DOCUMENTS

| EP | 1 110 529 A1 | 6/2001 |
|---|---|---|
| JP | 2004-508138 A | 3/2004 |
| RU | 2 269 991 | 2/2006 |
| WO | WO 91/08725 A1 | 6/1991 |
| WO | WO 02/22062 A1 | 3/2002 |
| WO | WO 2005/007052 A1 | 1/2005 |
| WO | WO 2006/037595 A1 | 4/2006 |

OTHER PUBLICATIONS

Form PCT/ISA/237 (Written Opinion of the International Searching Authority) dated Jun. 22, 2007.

Form IPEA/408 (Written Opinion of the International Examining Authority) dated Sep. 17, 2008.

Form IPEA/409 (International Preliminary Report on Patentability) dated Dec. 22, 2008.

English language translation of Notice of Reasons for Rejection dated Dec. 13, 2011 issued in the corresponding Japanese Patent Application No. 2009-529539.

\* cited by examiner

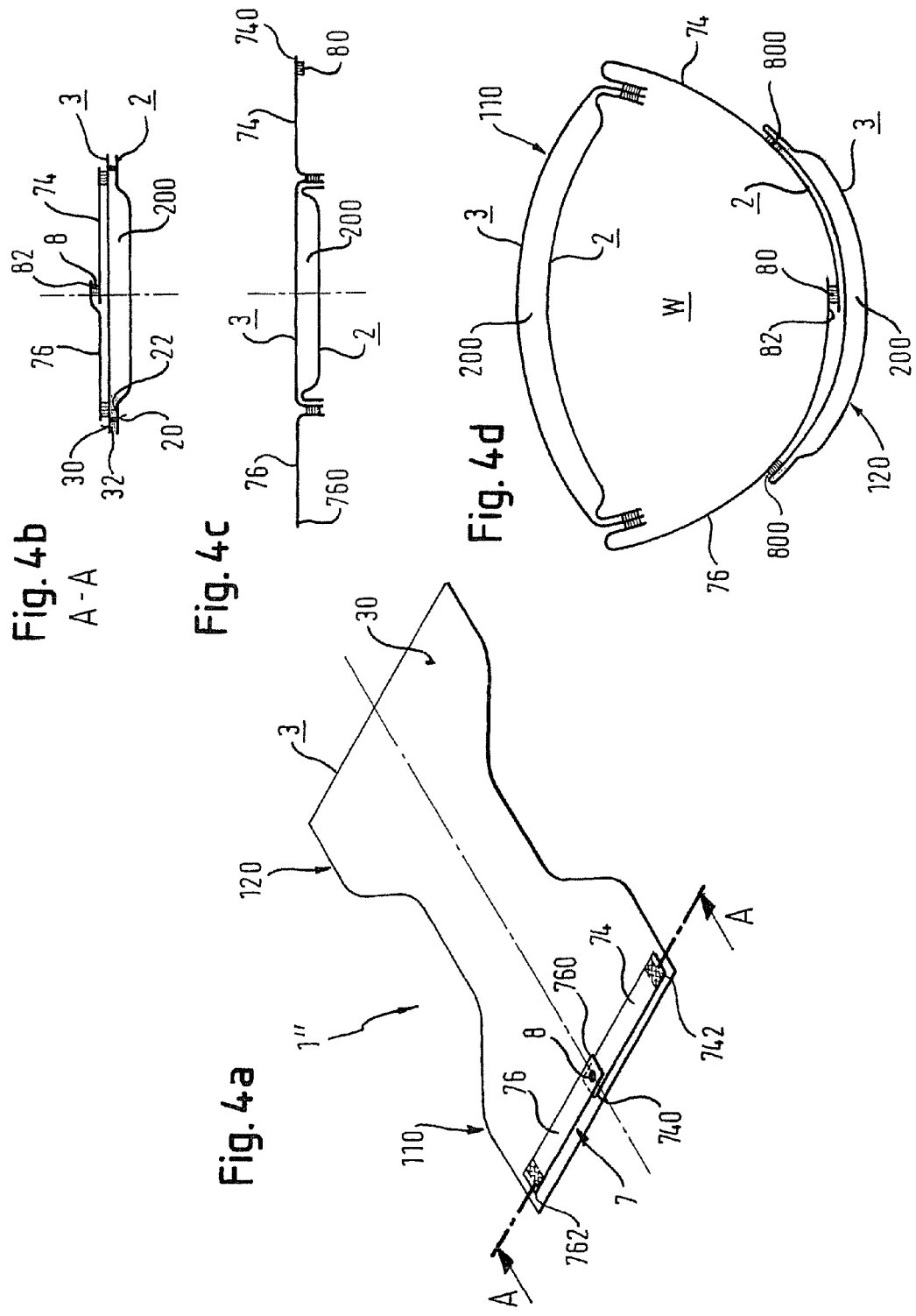

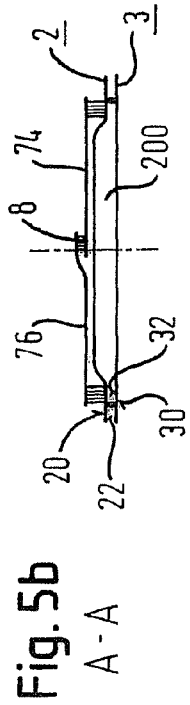
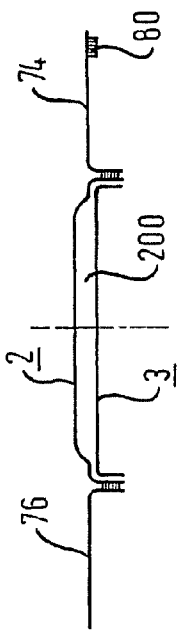
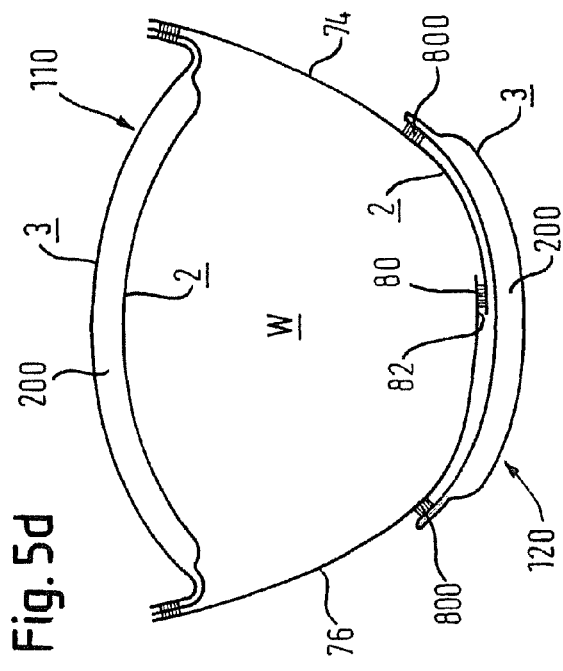
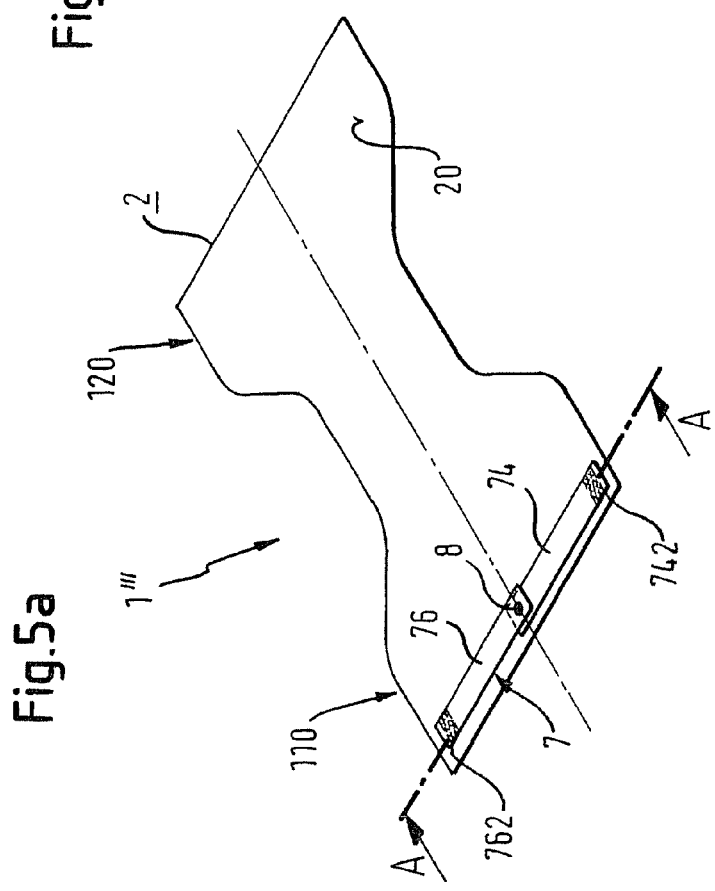

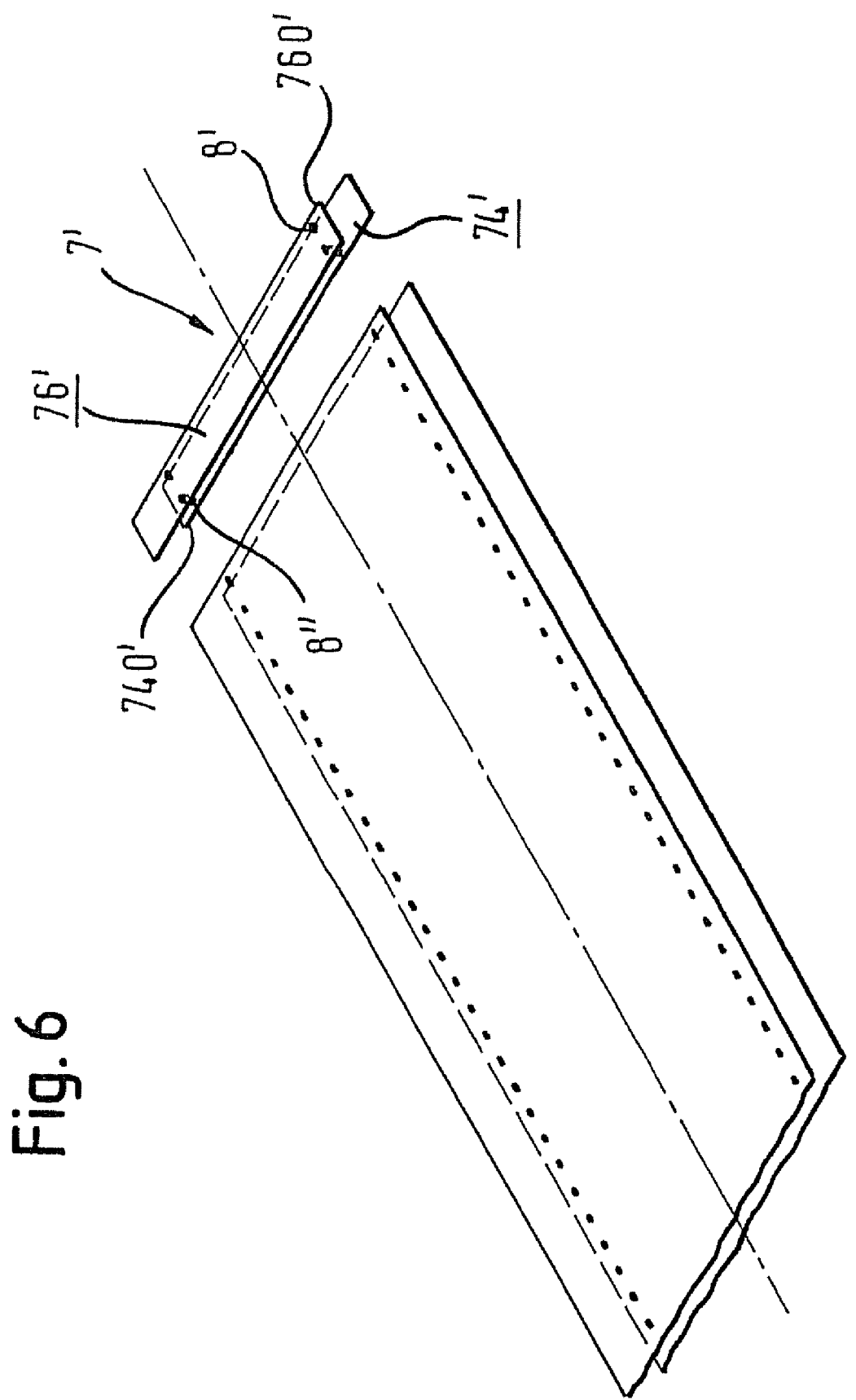

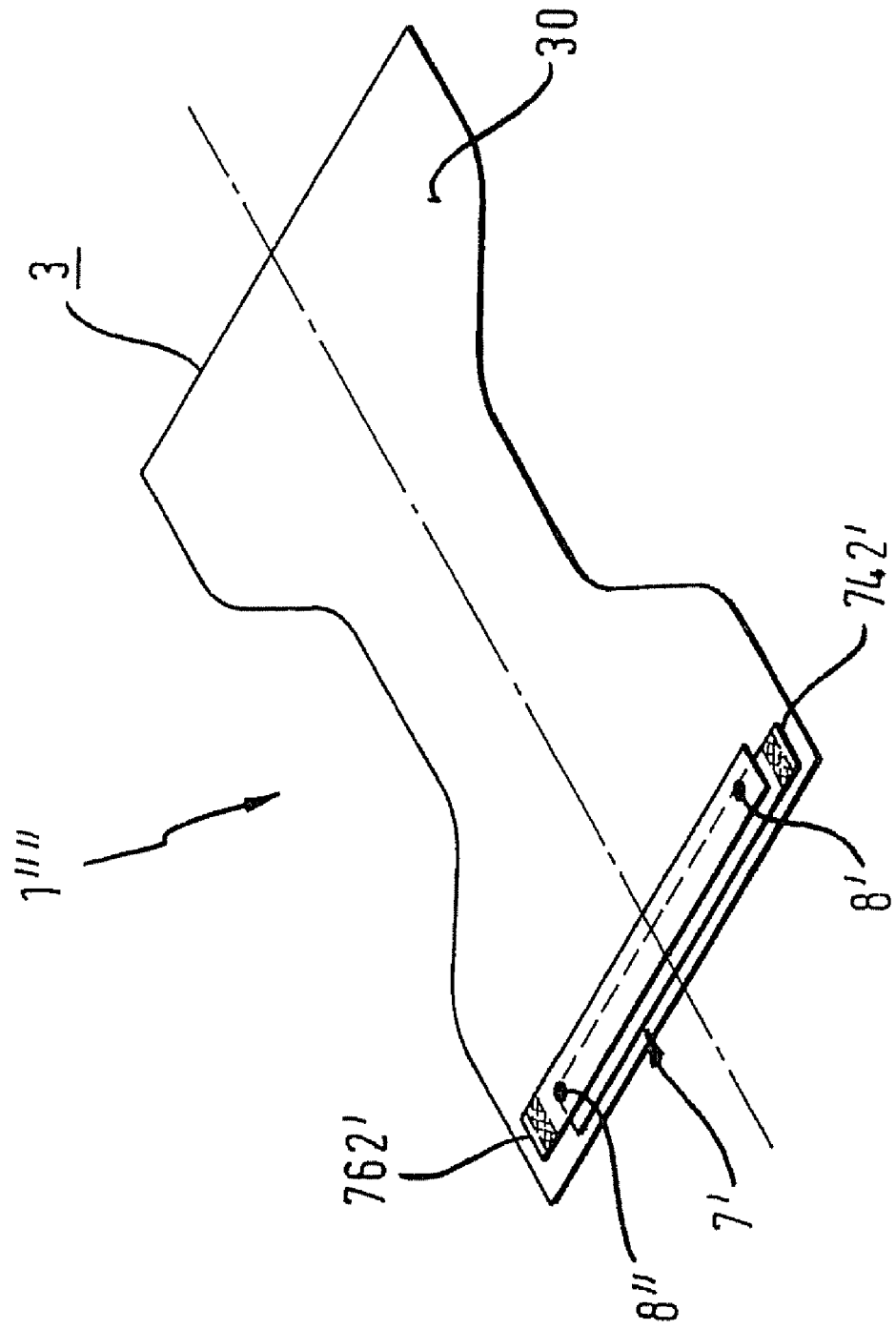

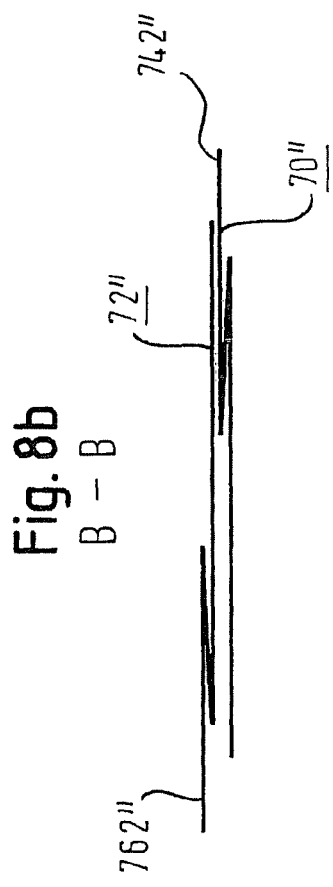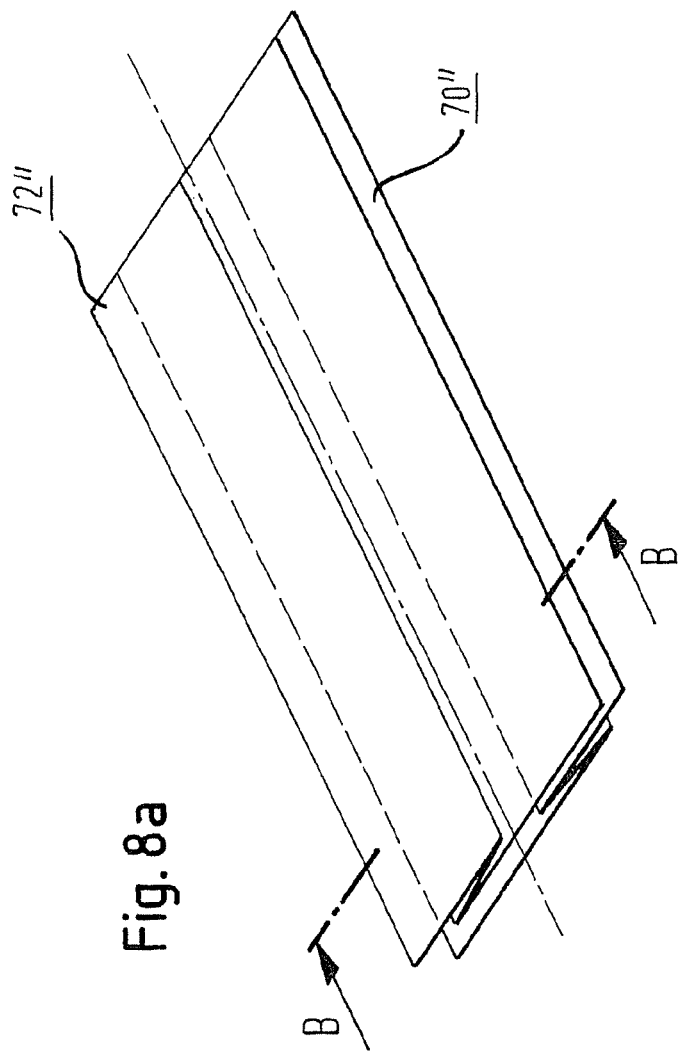

ABSORBENT ARTICLE, BELT STRUCTURE, MANUFACTURING METHOD FOR A BELT STRUCTURE AND MANUFACTURING METHOD FOR AN ABSORBENT ARTICLE

TECHNICAL FIELD

The invention relates to an absorbent article, a belt structure, a manufacturing method for a belt structure and a manufacturing method for an absorbent article.

TECHNOLOGICAL BACKGROUND

In the field of absorbent articles, in particular in the field of baby diapers, napkins and incontinence products, there is a constant need of improvements with regard to the production efficiency as these products are staple products and are manufactured in large scale. Absorbent articles of this kind usually comprise a top-sheet, a back-sheet and an absorbent core situated between the two sheets of the absorbent article. The top-sheet and the absorbent core are intended to be directed towards the wearer when the absorbent article is worn.

Recent developments in the field of fastening structures for absorbent articles require the use of elongate belts in order to fasten the absorbent article around the waist of a wearer. This is, in particular, the case in the field of incontinence products, where the fastening structures of the absorbent articles need to accommodate varying sizes of the mainly adult wearers. The elongate belts of these fastening structures can exhibit reasonably long lengths such that the handling of the belts is difficult from a production and packaging point of view. The belts of the conventional fastening structures usually extend from the top-sheet and/or the back-sheet of the absorbent articles in the lateral direction, which may lead to the unwanted effects described in the following. In particular, the lengthy belts can pose a limitation on the manufacturing speed of a production line of the absorbent articles and are a constant risk to the production line in terms of blocking a machine or becoming caught or jammed in a production apparatus. When it comes to packaging the manufactured articles, there is the danger that the belts of two or more of the absorbent articles become entangled with one another, which slows down the production efficiency.

Additionally, the handling of two separate lengthy belts in the manufacturing process is time and cost consuming since each of the belts needs to be arranged and orientated properly before it can be attached to the absorbent article.

Conventionally, the belts are attached to the absorbent article by inserting them between the top-sheet and the back-sheet in order to enhance the stability of the respective bonding. This renders the attachment process of the belts even more difficult since the belts have to be arranged and positioned properly and then inserted between the top-sheet and the back-sheet.

SUMMARY

Accordingly, it is an object of certain embodiments of the present invention to provide an absorbent article and a method for its manufacture that permits improvements of the belt handling during the manufacturing process and, in particular, an absorbent article which is made to improve the production efficiency and enables production at a high production rate. A further object is to provide a belt structure and a method for its manufacture that can be used to increase the production efficiency when producing absorbent articles.

The above-mentioned objects are solved by an absorbent article with the features described below.

Accordingly, the absorbent article comprises a top-sheet having an inner side and an outside and a back-sheet having an inner side and an outside, the inner side of the back-sheet being directed towards the inner side of the top-sheet. At least one elongate belt is provided which has a free end portion for fastening the absorbent article around the waist of a wearer and an attachment end portion that is fixedly attached to the outside of the back-sheet or to the outside of the top-sheet. Furthermore, the free end portion is arranged within the boundaries of the top-sheet and/or the back-sheet.

The term "boundaries" could also be referred to as the "footprint" of the top-sheet and/or the back-sheet which corresponds top the spatial extension of the respective sheets in their main plane.

It is to be understood that the term "free end portion" relates to the portion of the elongate belt that is not fixedly attached to the back-sheet and/or the top-sheet. The free end portion can be moved freely and independently of the rest of the absorbent article in order to tie the belt around the waist of a wearer. The free end portion is in particular "free" when the absorbent article is in the process of its positioning on the wearer. However, the term is not to be construed to mean that the free end portion is always free to move. It is, in fact, secured to the absorbent article when the article is in the correct wearing position and can also be attached to the absorbent article during manufacture, packaging and storage.

This specific arrangement, especially the arrangement of the elongate belt, contributes to an increase in the production efficiency. In particular, the attachment of the elongate belt on the outside of the top-sheet or on the outside of the back-sheet enables an easy attachment since, unlike in conventional absorbent articles, complicated belt handling for inserting a conventional belt between the top-sheet and the back-sheet is no longer necessary. Accordingly, the belt is fixed on the outside of the top-sheet or the outside of the back-sheet.

Furthermore, by arranging the free end portion within the boundaries of the top-sheet and/or the back-sheet, it is ensured that the belt does not extend beyond the boundaries of the top-sheet and/or the back-sheet, in particular not during the production process and/or a packaging process. This is particularly advantageous in fast production lines because the belts are not prone to entanglement, do not clog or jam the machinery, and the outer dimensions of the produced absorbent article are clearly defined. It is even contemplated that the dimensions of a production line could be reduced in the cross-machine direction since the belts do not extend beyond the boundaries of the back-sheet and/or the top-sheet. More narrow machines and production lines result in easier access to the components of the production line for the production operators. This may result in safer working conditions for the operators. In addition to that, narrower production lines usually have a reduced footprint compared to wider ones and, thus, safe space in a production hall.

It is obvious that the elongate belts can be extended beyond the boundaries of the top-sheet and/or the back-sheet by a user when the absorbent article is used. This is in particular the case when the absorbent article is applied to a wearer by extending the elongate belts around the hip of the wearer. The user, which can be a different person from the wearer, grips the belts and pulls them in the desired application direction. In other words, the arrangement of the elongate belts within the boundaries of the top-sheet and/or the back-sheet is particularly present before the article is used, but not necessarily when the article is used and/or worn.

The expression "before the absorbent article is used" indicates any time before a user and/or wearer actually grips the elongate belt, or the free end portion of the elongate belt, to fasten the absorbent article around the waist of a wearer. Particularly, it indicates the time between the instant of the actual manufacture of the absorbent article, in particular, the moment of attaching the elongate belt to the top-sheet or the back-sheet, and the instant in which the elongate belt is gripped, touched and/or opened by a user for the first time in order to apply the absorbent article to a wearer.

In an advantageous embodiment, a pair of elongate belts is fixedly attached to the outside of the back-sheet or the outside of the top-sheet. A pair of elongate belts provides greater flexibility with regard to the actual fastening process of the absorbent article around the waist of a wearer.

When two elongate belts are attached to the absorbent article, the free end portion of the first elongate belts is preferably directed towards the attachment end portion of the second elongate belt and vice versa. In other words, the free ends of the belts are situated within the boundaries of the top-sheet and/or the back-sheet such that the belts extend from the outer portions of the absorbent article towards the inner portions of the absorbent article.

In order to provide an efficient absorbent article, an absorbent core may be situated on the inner side of the back-sheet and is intended to be directed towards the wearer when the absorbent article is worn.

The attachment end portion of the elongate belt can be longitudinally spaced apart from the free end portion of the elongate belt. In other words, the attachment end portion is not situated in the middle of the elongated belt. This arrangement of the elongate belts provides the advantage that the entire extension of the elongate belts can be used to apply the elongate belt to a wearer.

In order to further improve the handling of the belts of the absorbent article and of the absorbent article itself during manufacture and during packaging when two elongate belts are attached to the absorbent article, the first elongate belt and the second elongate belt are fixedly attached to the outside of the top-sheet or the outside of the back-sheet at the attachment end portions and the elongate belts overlap in the regions of the free end portions before the article is used. This overlap of the free end portions of the first and second elongate belts provides an improved handling since a greater length of the belt can be positioned inside the boundaries of the top-sheet and/or the back-sheet of the absorbent article.

It is particularly advantageous when the first elongate belt and the second elongate belt are fastened or secured or pegged together with at least one breakable bond in the overlap. This breakable bond in the overlap of the free end portions ensures that the free end portions of the elongate belts do not move around and are prevented from leaving the area defined by the boundaries of the top-sheet and/or the back-sheet of the absorbent article. In other words, before the article is used, any potentially dangling loose ends of the free end portions of the elongate belts are appropriately fastened such that the free ends are confined to one specific location or area within the boundaries of the top-sheet and/or the back-sheet of the absorbent article.

The term "breakable bond" as it is used herein indicates a bond between the two elongate belts that, on the one hand, can be easily broken by a user by simply pulling apart one belt from the other but, on the other hand, is strong enough to withstand any forces acting on the belts during the manufacturing process. Such a bond can be formed, for example, by a hook and loop fastener (Velcro fastener) arrangement or by a combination of an adhesive patch and a plastics film, in particular a PE-film. The previously mentioned arrangements have the advantage that they can be re-fastened should this be desired. However, any other suitable material and/or method can be used to form the breakable bond, in particular adhesives or spot welding which lead to a bond that cannot be re-fastened once it has been broken.

The spatial confinement of the first and second elongate belts can be further improved by also attaching at least one of the free end portions to the back-sheet or the front sheet by at least a breakable bond.

In order to accommodate longer belt lengths, it is preferable to fold at least one of the elongate belts in order to wrap up a length of the elongate belt. Folding the belts ensures that even longer belts can be confined within the boundaries of the top-sheet and/or the back-sheet. In this context, it is particularly advantageous to fold the elongate belt in a Z-shape such that the front end of the free end portion is situated in the direction of the longitudinal extension of the belt and spaced apart from the attachment end portion, such that a user can easily grasp the free end portion. This arrangement is also more intuitive for a user since the free end portion of the belt extends in the direction in which the user expects it to unfold.

In connection with a folded belt and, in particular, in connection with a belt folded in a Z-shape, it can be advantageous to use more than one breakable bond to also attach several folded portions of the belt to the belt itself or to the respective other belt.

In an advantageous embodiment, the longitudinal extension of the elongate belt is equal to, or is longer than the maximum lateral extension of the top-sheet and/or the back-sheet. The arrangement of the elongate belt as described above is particularly advantageous with reasonably long belts, in particular belts of the length being equal to, or longer, than the maximum lateral extension of the back-sheet and/or the top-sheet because any clogging or jamming of the production and/or packaging lines can be prevented. Longer belts can be more comfortable to wear for a wearer under certain circumstances.

The above-mentioned objective is also solved by a belt structure described below.

Accordingly, the belt structure comprises a first elongate belt and a second elongate belt for fastening the absorbent article around the waist of a wearer. Furthermore, the first elongate belt and the second elongate belt are provided with an attachment end portion each, whereas the attachment end portion is arranged to be fixedly attached to the absorbent article. Additionally, the first and second elongate belts have a free end portion for fastening the absorbent article around the waist of a wearer. The free end portion of the first elongate belt and the free end portion of the second elongate belt overlap and are fastened to one another by at least one breakable bond.

The described belt structure resembles that described above with regard to the absorbent article. It has the advantage of providing a compact and easy to handle belt structure that can be attached to an absorbent article without any complicated adjustment and orientation operations. Furthermore, both belts of the belt structure can be handled as one piece and, in particular, can be attached the absorbent article as this very one piece. The handling of two belts as one piece reduces the number of steps required for manufacturing the absorbent article as well as the reliability of the attachment.

Furthermore, the free end portions of the belts are overlapped and fastened to one another. Accordingly, the free end portions of the belts are spatially confined and, thus, reduce the risk of the free end portions becoming entangled with one another or that they block the production line when an absorbent article with the belt structure attached to it is fed through a production line. This is due to the fact that the free end portions of the elongate belt are held together and in place by the breakable bond.

In a preferred embodiment, the first elongate belt and the second elongate belt overlap such that substantially all of the belt material overlaps, except for the attachment end portion. The attachment end portion substantially comprises the longitudinal extension of an attachment bond and a seam allowance. A belt structure with these features has the advantage that a great length of belt material can be handled easily. Nevertheless, since the attachment end portion has a longitudinal extension of substantially the attachment bond plus a seam allowance, the belt structure can be securely fastened to the top-sheet or the back-sheet of the absorbent article. The seam allowance ensures a secure attachment of the belt material to the absorbent article. Preferably, the attachment end portion of the first and second elongate belts is made from a single layer of belt material, e.g. from a single layer of back-sheet material.

In another embodiment, the first elongate belt and the second elongate belt overlap substantially only at the breakable bond which fastens or pegs or secures together the first and the second elongate belts. This provides for the superior handling advantages of the belt structure even for shorter belts.

In a further preferred embodiment, the first elongate belt and/or the second elongate belt are at least folded once in order to wrap up a length of the first and/or second elongate belt. The provision of this fold enables a reduction of the actual outer dimensions, in particular its length in the longitudinal direction, of the belt structure. In other words, the fold makes it possible to use relatively long belts that can still be handled easily as the composite set of the belt structure.

Other embodiments of the belt structure are similar to that as described above with regard to the absorbent article.

The present disclosure furthermore relates to a manufacturing method for a belt structure to be attached to an absorbent article.

The manufacturing method comprises the steps of providing a first web and a second web of belt material of a width corresponding to the length of the belts to be manufactured, overlapping the first and the second webs, fastening the first and the second web together with at least one breakable bond, and cutting the belt structure from the composite of the fastened together first and second webs.

This manufacturing method has the advantage of providing a belt structure that can be attached to an absorbent article in a reliable and efficient way. By providing the first and second webs of belt material, the belt material can be delivered on a roll of material of a width that corresponds to the length of the belts to be manufactured.

The term "width" of the web as it is used herein relates to the extension of the web in the cross-machine direction. In other words, the belts of the final belt structure have a length that corresponds to the extension of the web in the cross-machine direction. The width of the finished belt corresponds to the length of the composite of the webs in the machine-direction that is cut from the continuous webs.

The manufacturing method includes the step of folding the first and/or the second web at least once before fastening the first and second webs together. This folding of the web is preferably done along the machine direction. In a preferred embodiment, the folding is carried out in a Z-shape in order to wrap up an even longer length of the resulting belt.

The disclosure, furthermore, relates to a manufacturing method for an absorbent article.

Accordingly, the method comprises the steps of providing an absorbent article with a top-sheet having an inner side and an outside and a back-sheet having an inner side and an outside, the inner side of the back-sheet being directed towards the inner side of the top-sheet. As a following step, at least one belt structure, as is described above, is attached to the outside of the back-sheet or the outer sheet of the top-sheet.

BRIEF DESCRIPTION OF THE DRAWINGS

FIG. 4a is a schematic perspective view of an absorbent article of a third embodiment, with the belt structure of FIG. 3 attached to the outside of the back-sheet of the absorbent article;

FIG. 4b is a schematic cross-section through the absorbent article of FIG. 4a along the line A-A in a configuration of the absorbent article before use;

FIG. 4c is a schematic cross-section through the absorbent article of FIG. 4a along the line A-A in a configuration of the absorbent article with unfolded belts;

FIG. 4d is a schematic cross-section through the absorbent article of FIGS. 4a to 4c, showing the absorbent article in a configuration in use, when fitted to a wearer;

FIG. 5a is a schematic perspective view of an absorbent article of a fourth embodiment, with the belt structure of FIG. 3 attached to the outside of the top-sheet of the absorbent article;

FIG. 5b is a schematic cross-section through the absorbent article of FIG. 5a along the line A-A in a configuration of the absorbent article before use;

FIG. 5c is a schematic cross-section through the absorbent article of FIG. 5a along the line A-A in a configuration of the absorbent article with unfolded belts;

FIG. 5d is a schematic cross-section through the absorbent article of FIGS. 5a to 5c, showing the absorbent article in a configuration in use, when fitted to a wearer;

FIG. 6 is a schematic perspective view of a second embodiment of a composite of two webs of belt material and of a belt structure cut from the composite material;

FIG. 7 is a schematic perspective view of an absorbent article with the belt structure of FIG. 6 attached to the outside of the back-sheet of the absorbent article;

FIG. 8a is a schematic perspective view of another embodiment of a composite of two webs of belt material;

FIG. 8b is a schematic sectional view of the composite of the two webs of belt material of FIG. 8a taken along line A-A.

DETAILED DESCRIPTION OF THE EXEMPLARY EMBODIMENTS

Figure 1:
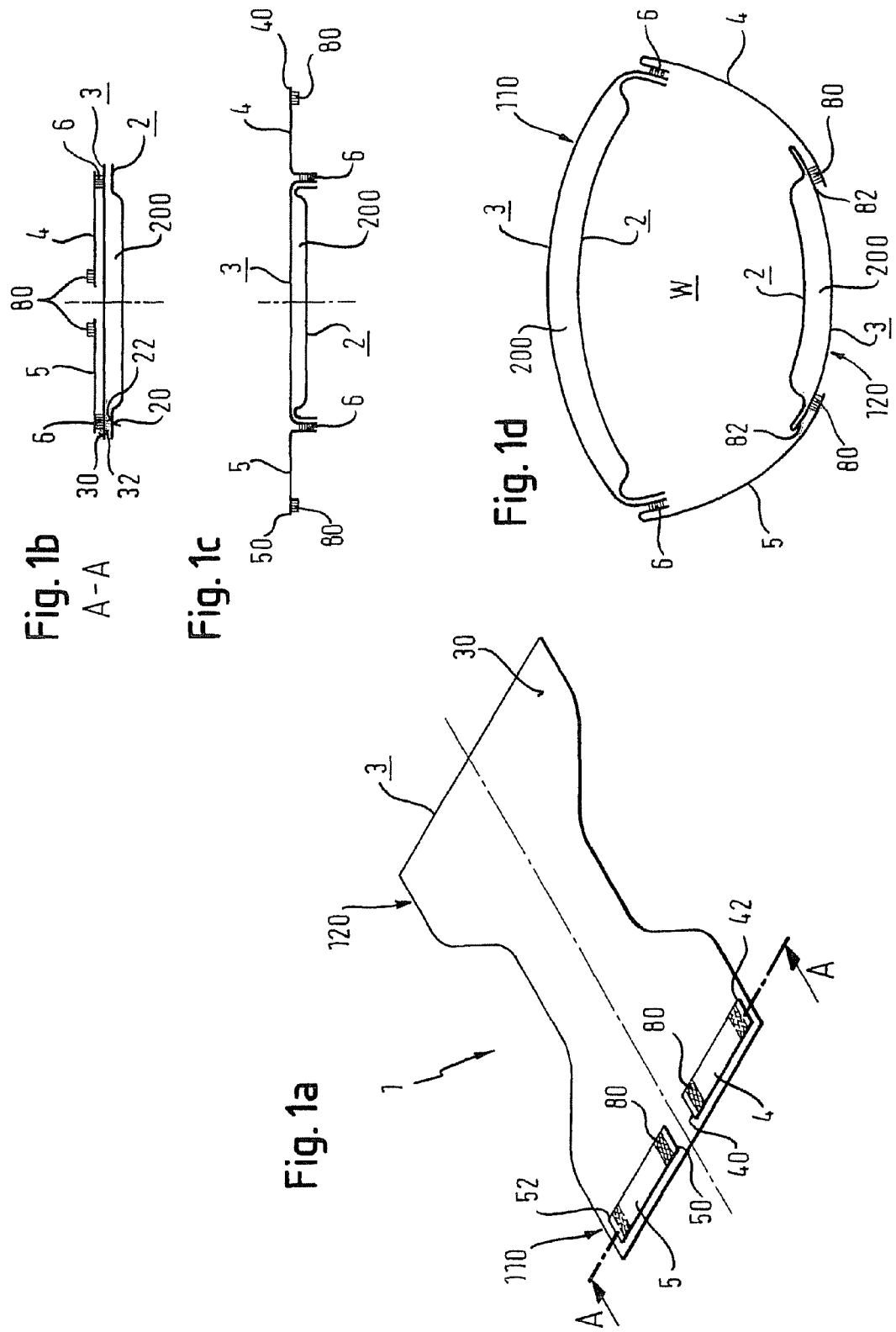
FIG. 1a is a schematic perspective view of an absorbent article in a first embodiment, showing the outside of the back-sheet of the absorbent article and a pair of elongate belts fixedly attached to the back-sheet.
FIG. 1b is a schematic cross-section through the absorbent article of FIG. 1a along the line A-A in a configuration of the absorbent article before use.
FIG. 1c is a schematic cross-section through the absorbent article of FIG. 1a along the line A-A in a configuration of the absorbent article with unfolded belts.
FIG. 1d is a schematic cross-section through the absorbent article of FIGS. 1a to 1c, showing the absorbent article in a configuration in use, when fitted to a wearer.
Figure 2:
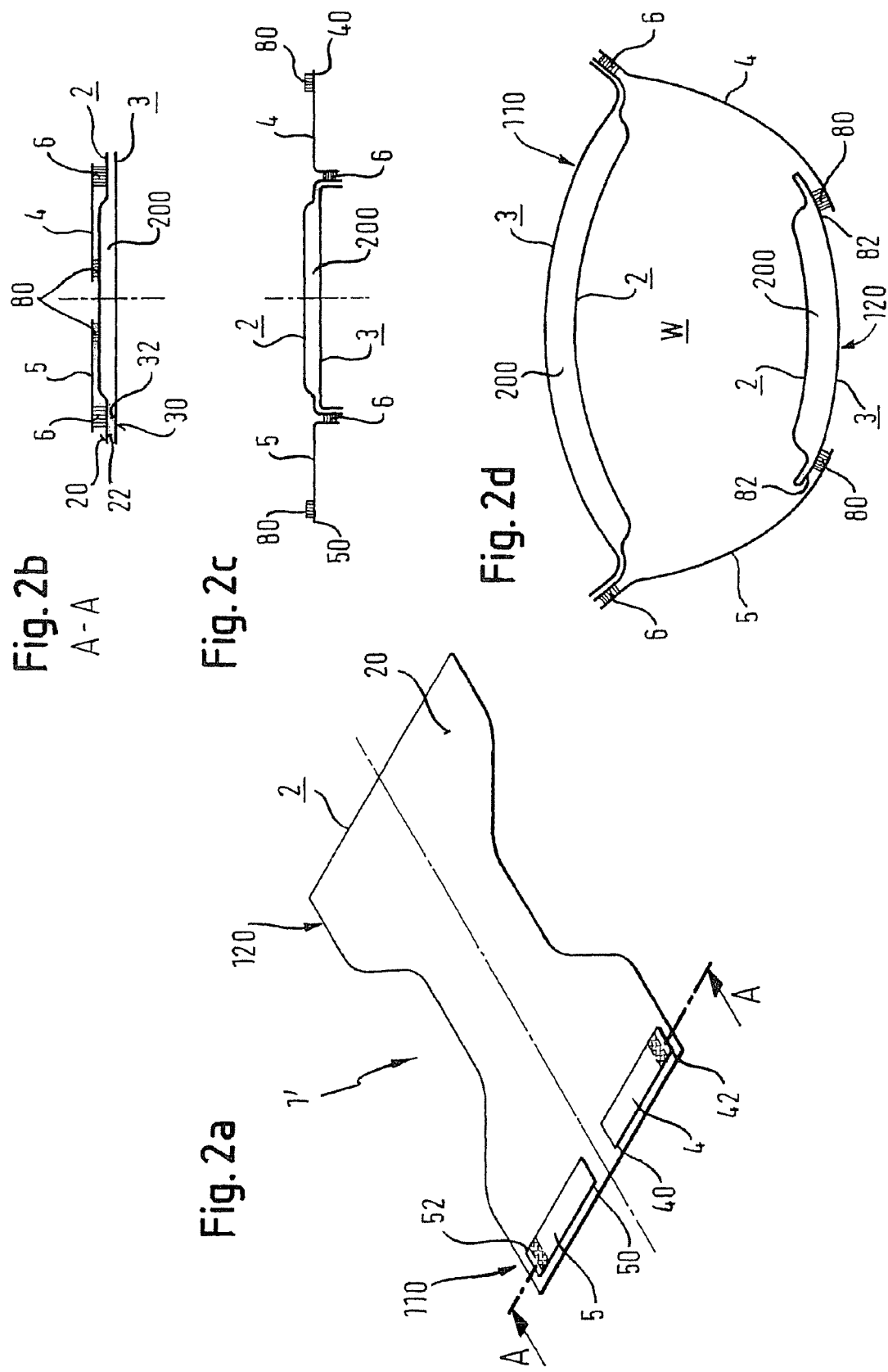
FIG. 2a is a schematic perspective view of an absorbent article in a second embodiment, showing the outside of the top-sheet of the absorbent article and a pair of elongate belts fixedly attached to the top-sheet.
FIG. 2b is a schematic cross-section through the absorbent article of FIG. 2a along the line A-A in a configuration of the absorbent article before use.
FIG. 2c is a schematic cross-section through the absorbent article of FIG. 2a along the line A-A in a configuration of the absorbent article with unfolded belts.
FIG. 2d is a schematic cross-section through the absorbent article of FIGS. 2a to 2c, showing the absorbent article in a configuration in use, when fitted to a wearer.

Various exemplary, but non-limiting, embodiments of the invention will now be described with references to the Figures.

In the following, preferred embodiments of the disclosure are described with reference to the Figures. Similar or identical elements carry the same reference numerals and repeated description of these features in the respective embodiments is omitted.

FIGS. 1a to 1d show a first embodiment of an absorbent article 1 in a schematic perspective view. The absorbent article 1 has a back-sheet 3, the outside 30 of which is visible in FIG. 1a. A first elongate belt 4 and a second elongate belt 5 are shown attached to the outside 30 of the back-sheet 3.

As can be seen in FIG. 1a, the back-sheet 3 is directed with its inner side 32 towards the inner side 22 of the top-sheet 2. The outside 20 of the top-sheet 2 is not directly attached to the first elongate belt 4 or the second elongate belt 5.

Between top-sheet 2 and back-sheet 3, an absorbent core 200 is situated which serves to absorb liquids that are introduced into the absorbent article 1. The absorbent core 200 is arranged on the inner side 22 of the top-sheet 2 as well as on the inner side 32 of the back-sheet 3, whereas top-sheet 2 and absorbent core 200 are intended to be directed towards the wearer when the absorbent article 1 is worn. The absorbent core 200 can be of any conventional kind. Examples of commonly occurring absorbent cores or absorbent materials are cellulosic fluff pulp, tissue layers, highly absorbent polymers (so called superabsorbent cores), absorbent foam materials, absorbent non-wovens and the like.

As can be seen in FIG. 1b in the cross-section taken along line A-A of FIG. 1a, the first elongate belt 4 and the second elongate belt 5 are situated on the outside 30 of the back-sheet 3 wherein the elongate belt 4 is fixedly attached to the back-sheet 3. The first elongate belt has a free end portion 40 for fastening the absorbent article 1 around the waist of a wearer, and an attachment end portion 42 for fixedly attaching the belt to the back-sheet 3 of the absorbent article 1 using an adhesive 6 or any other attachment means or methods such as ultrasonic bonding or heat-welding. The free end portion 40 of the elongate belt 4 is longitudinally spaced apart from the attachment end portion 42 of the elongate belt 4. In other words, the free end portion 40 represents one end of the first belt 4, and the attachment end portion 42 represents the other end of the elongate belt 4 in the longitudinal direction of the elongate belt.

The second elongate belt 5 likewise has a free end portion 50 and an attachment end portion 52 which have a similar structure as in the first elongate belt 4.

FIG. 1a shows that the first elongate belt 4 and the second elongate belt 5 are situated and arranged on the outside 30 of the back-sheet 3 of the absorbent article 1 such that the free end portions 40, 50 of the first elongate belt 4 and the second elongate belt 5 are arranged within the boundaries of the back-sheet 3. The boundaries of the back-sheet 3 are defined by the actual outline of the back-sheet 3 (or the top-sheet 2), which could also be referred to as the "footprint" of the back-sheet 3 (or top-sheet 2).

In the embodiment shown in FIGS. 1a to 1d, the free end portion 40 of the first elongate belt 4 is directed towards the attachment end portion 52 of the second elongate belt 5, and the free end portion 50 of the second elongate belt 5 is directed towards the attachment end portion 42 of the first elongate belt 4. Accordingly, the first free end portion 40 and the second free end portion 50 are situated opposite one another.

FIG. 1c shows the absorbent article in a state when its belts are unfolded, namely, when the first elongate belt 4 and the second elongate belt 5 are laterally stretched apart from one another such that the free end portions 40, 50 extend in opposite directions. To achieve this configuration, a user may have gripped the belts 4, 5 in order to fasten the absorbent article 1 around the waist of a wearer.

As can be seen in FIG. 1c, due to the attachment positions of the first elongate belt 4 and of the second elongate belt 5, the outer ends of the top-sheet 2 and the back-sheet 3 are bent downwardly as a result of the initial orientation of the belts towards one another. This is due to the improved handling of the belts 4, 5 during the production process.

In FIG. 1d, a schematic cross-section of the absorbent article 1 is shown in a configuration when it is in use, in particular when it is fitted to a wearer. In the Figure, a "W" is placed in the position where the cross-section of a wearer would be situated in order to show the position of a wearer. In the following, "W" will symbolise the position of a wearer. In particular, in the lower part of FIG. 1d, a front portion 120 of the absorbent article 1 is shown, whereas in the upper part of the Figure, a rear portion 110 of the absorbent article 1 is shown. The terms "front portion" and "rear portion" are relative terms and do not necessarily mean that the front portion has to be worn on the front side of the wearer.

As the belts 4, 5 that are basically situated on the rear portion 110 of the absorbent article 1, need to be fastened around the waist of the wearer W and subsequently need to be secured to the front portion 120 of the absorbent article 1 in order to secure the absorbent article to the wearer W, fasteners 80 are present on the free end portions 40, 50 of the belts 4, 5.

The fasteners 80 can be of any known kind. In particular, the fasteners 80 on the belts 4, 5 can be hooks of hook and loop fasteners, whereas the loops are provided on a landing zone 82 on the outside 30 of the back-sheet 3 on the front portion 120 of the absorbent article 1. The fasteners 80 could also be adhesive pads that interact with a landing zone 82 made from a PE-film on the outside 30 on the front portion 120 of the back-sheet 3. In a particularly advantageous embodiment, the back-sheet 3 is made from a material that also serves as a landing zone 82. Such a material for the back-sheet 3 includes, but is not limited to, a non-woven with a loop structure or a plastics film, in particular a PE-film.

When turning now to a second embodiment of the absorbent article 1' which is shown in FIGS. 2a to 2d, it becomes apparent that the second embodiment is widely identical with the first embodiment such that lengthy descriptions of similar features are omitted. However, it will be readily appreciated that the fundamental difference between the first embodiment of the absorbent article of FIGS. 1a to 1d and the second embodiment shown in FIGS. 2a to 2d is that the elongate belts 4, 5 are fixedly attached to the outside 20 of the top-sheet 2 in the second embodiment instead of being fixedly attached to the back-sheet 3 in the first embodiment. Accordingly, the free end portions 40, 50 are folded in the opposite direction compared to the situation shown in FIGS. 1a to 1d. As will be seen in the following, this is also a very viable solution which can, from a production point of view, be the preferred embodiment.

In particular, FIG. 2c shows that the outer ends of the top-sheet 2 and the back-sheet 3 are not as much bent downwardly as in the first embodiment which may result in a more comfortable fit for the wearer, in particular when the wearer is a bedridden person. This lesser bending is a result of fixedly attaching the belts 4, 5 to the top-sheet 2 rather than to the back-sheet 3.

Furthermore, as can be seen in FIGS. 2b and 2d, the fasteners 80 can be used in two different ways, namely on the one hand to fasten the free ends 40, 50 of the belts 4, 5 to the top-sheet 2 when the absorbent article 1' is manufactured and distributed and on the other hand the same fasteners 80 can be used to fasten the belts 4, 5 around the waist of the wearer W and attach the free ends 40, 50 to the landing zones 82 on the front portion 120 of the absorbent article 1'. This is also advantageous since the fasteners 80 are protected during packing and distributing procedures and during storage as they are directed towards the inside.

Figure 3:
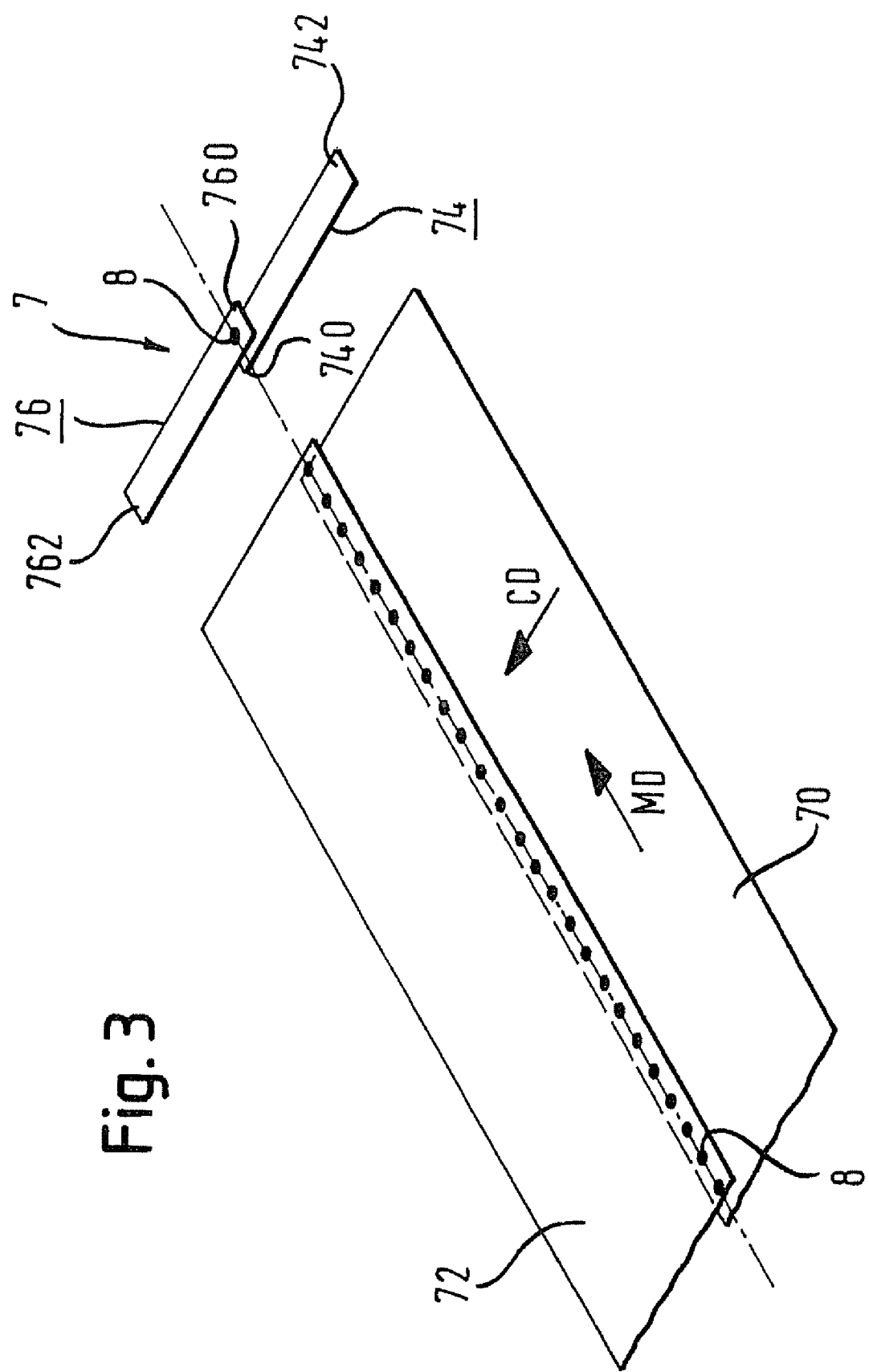
FIG. 3 is a schematic perspective view of an embodiment of a composite of two webs of belt material and of a belt structure cut from the web composite.

FIG. 3 shows a belt structure 7 that comprises a first belt 74 and a second belt 76 that have attachment end portions 742, 762, and free end portions 740, 760 respectively. Unlike the embodiments shown in FIGS. 1a to 2d, the free end portions 740, 760 of the two belts 74, 76 overlap and are fastened or secured or pegged together by a breakable bond 8 in the section of the overlap. Although this breakable bond 8 can be an adhesive or a weld that cannot be re-fastened after it has been broken, it is preferred that the breakable bond 8 is a bond that can be re-fastened, in particular a hook and loop fastener arrangement or a combination of an adhesive patch and an PE-film.

The belt structure 7 is made by cutting it from a composite of a first web 70 and a second web 72. The first web 70 and the second web 72 both have a width in the cross-machine direction CD that substantially corresponds to the length of the finished belts 74, 76 of the belt structure 7. If different lengths of the belts in the belt structure 7 are required, webs 70, 72 of different widths can be used, as it will become apparent with regard to the embodiments described below.

The webs 70, 72 are provided in an overlapping manner and breakable bonds 8 are formed between the overlapped webs 70, 72 to fasten them together before the belt structure 7 is actually cut from the composite of the webs 70, 72. It is to be noted that the breakable bonds 8 in this embodiment are aligned in only one row extending in the longitudinal direction of the webs 70, 72, i.e. in the machine direction MD. In particular, the overlap of the two webs 70, 72 comprises only a small portion of the entire length of the finished belt structure 7. However, a structure with two rows of breakable bonds 8 is shown in the embodiments of FIGS. 6 to 9 below. Naturally, any suitable number of rows of breakable bonds 8 can be used.

The manufacture of the belt structure 7 in this embodiment can be carried out in a reliable manner, namely by overlapping the first web 70 of belt material and the second web 72 of belt material and fastening the first web 70 and the second web 72 together by the breakable bonds 8. The composite of the first web 70 and the second web 72 is then cut in stripes to provide the belt structure 7.

Accordingly, the composite of the first web 70 and the second web 72 can be easily guided and fed in the machine-direction MD and can be carried towards a cutting mechanism in order to cut the belt structure 7. The composite can also be pre-manufactured and delivered to the actual production line of the absorbent articles in roll form. This handling of the belt structures 7 is a considerable improvement compared to the case in which belts are delivered as single belts.

FIGS. 4a to 4d show a third embodiment of an absorbent article 1" with the belt structure 7 of FIG. 3 attached to it. The absorbent article 1" has a back-sheet 3 and the belt structure 7 is fixedly attached to the outside 30 of the back-sheet 3 in the section of the attachment end portions 742, 762 of the belt structure 7.

As will be appreciated, the attachment process of the belt structure 7 to the absorbent article 1" can be carried out reliably and without the need of extensive orientation of the belt structure 7. In particular, the belt structure 7 can be placed on the outside 30 of the back-sheet 3 and then fixed to the back-sheet 3 by simply fixedly attaching the attachment end portions 742 and 762 to the back-sheet 3.

Due to the breakable bond 8 between the first elongate belt 74 and the second elongate belt 76, the free end portions 740, 760 of the belt structure 7 are securely held in place during the attachment process as well as during any later manufacturing or packaging process of the absorbent article 1". This can be appreciated particularly well with reference to FIG. 4b, which shows a cross-section of FIG. 4a along the line A-A in FIG. 4a. Accordingly, the first elongate belt 74 and the second elongate belt 76, in particular their free ends 740, 760, cannot move around freely but are confined to their position relative to the back-sheet 3.

FIG. 4d shows the absorbent article 1" fastened around a wearer W. It will be appreciated that the fastening process is considerably different from that in the embodiments shown in FIGS. 1a to 2d.

In particular, the fastener 80 used for securing the belts 74, 76 around the waist of a wearer W secures the belts 74, 76 to one another. After the belts 74, 76 are secured to one another, the front portion 120 of the absorbent article 1" is secured to the connected belts 74, 76 using additional fasteners 800 which are situated on the top-sheet 2 of the front portion 120 of the absorbent article 1".

In a particularly advantageous embodiment, the breakable bond 8 serves at the same time as the fastener 80 for fastening the belts together. In particular, the breakable bond 8 can be a hook and loop connector or an adhesive pad attached to a landing zone made from a PE film and, after breaking the bond as it is shown in FIG. 4c, and re-fastening the belts 74, 76 together as it is shown in FIG. 4d, the breakable bond 8 is re-used as the fastener 80. In the embodiment shown in FIGS. 4a to 4d, however, at least one side for the attachment of the belts 74, 76 changes when the belts 74, 76 are moved from the position of FIG. 4b to the position of FIG. 4d. Accordingly, a landing zone 82 is provided on a side of the belts 74, 76 that is not involved in the bonding with the breakable bond 8.

It will be appreciated that in an embodiment not shown, the structure in the securing position could be different with the belts secured to the outside 30 of the back-sheet 3 in the same manner as it is described with regard to the embodiments shown in FIGS. 1a to 2d.

A fourth embodiment of the absorbent article 1''', which is shown in FIGS. 5a to 5d, is widely similar to the third embodiment. However, as will be readily appreciated, the belts 74, 76 are fixedly attached to the top-sheet 2 in the fourth embodiment in contrast to the attachment to the back-sheet in the third embodiment.

This attachment of the belts 74, 76 to the top-sheet 2 has some advantages over attaching the belts 74, 76 to the back-sheet 3. In particular, as can be seen in FIG. 5d, the bending of the outer sections of the top-sheet 2 and the back-sheet 3 is considerably reduced.

Furthermore, the fastener 80 can be made identical with the breakable bond 8 and no additional landing zone 82 is required, as the layering of the belts 74, 76 at the breakable bond 8 and the layering of the belts 74, 76 at the securing step is identical.

FIGS. 6 and 7 show a different embodiment of a belt structure 7'. The belt structure 7' is basically identical to that shown in FIGS. 4a to 5d with the exception that the belts 74', 76' overlap almost over their entire longitudinal length. Furthermore, two breakable bonds 8' and 8" are used to reliably fasten or secure or peg the two belts together, instead of using only one breakable bond 8. In particular, the breakable bonds 8' and 8" are situated in the free end portions 740' and 760' of the first elongate belt 74' and the second elongate belt 76'.

FIG. 7 shows an absorbent article 1"" with the belt structure 7' attached to the outside 30 of the back-sheet 3 of the absorbent article 1"". In this configuration, it is particularly easily recognizable that the attachment end portions 742' and 762' have a relatively small longitudinal extension, namely an extension that is only as long as the attachment bonding itself plus a small seam allowance.

The embodiment of the absorbent article 1"" of FIG. 7 allows providing an absorbent article with relatively long elongate belts 74', 76' that are still situated within the boundaries of the back-sheet 3 of the absorbent article and no loose ends.

Figure 9:
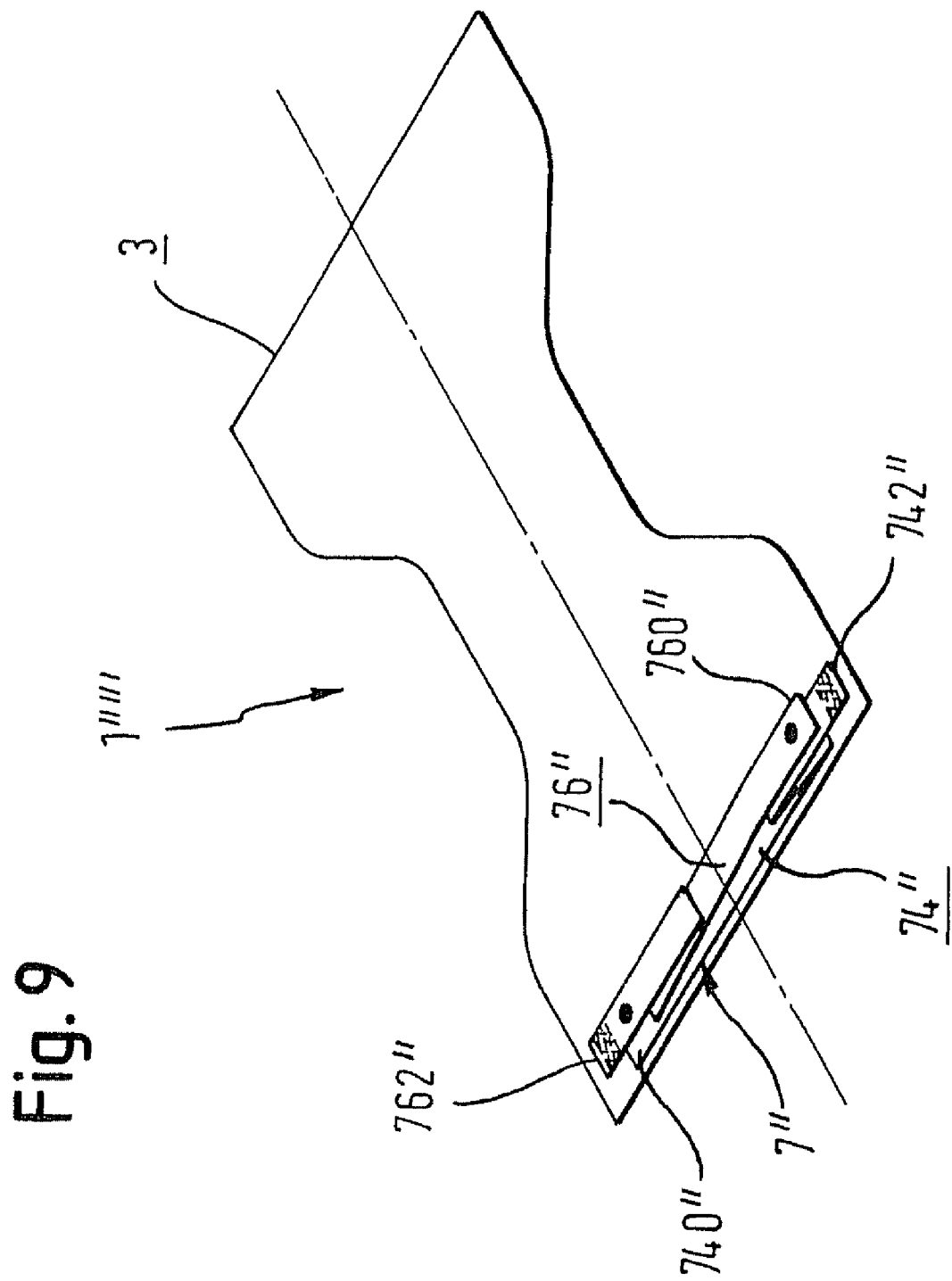
FIG. 9 is a schematic perspective view of an absorbent article with the belt structure of FIGS. 8a and 8b attached to the outside of the back-sheet of the absorbent article.

FIGS. 8a, 8b and 9 show yet another embodiment of the present disclosure. FIG. 8a shows a composite of two webs 70", 72" which are each folded in a Z-shape. This is clearly shown in FIG. 8b, which is the cross-section taken along the line B-B of FIG. 8a. The Z-shape of the folding of the two webs enables an even larger amount of belt material to be folded away to maintain the distance between the two attachment end portions 742" and 762" in order to attach the belt structure to an absorbent article 1""', as it is shown in FIG. 9. The maximum possible extension between the attachment end portions 742" and 762" is determined by the lateral extension of the back-sheet 3 and/or the top-sheet of the absorbent article 1""'.

The embodiment of FIG. 9 shows the belt structure 7" attached with its attachment end portions 742" and 762" to the back-sheet 3 of the absorbent article 1""'.

It is appreciated that an even larger amount of folds can be used in order to fold a desired amount of belt material such that the entire belt and in particular the free end portions 740" and 760" are situated within the boundaries of the back-sheet 3 or a top-sheet.

The invention claimed is:

1. An absorbent article comprising:
 a top-sheet having an inner side and an outside and a back-sheet having an inner side and an outside, the inner side of the back-sheet being directed towards the inner side of the top-sheet;
 a first elongate belt and a second elongate belt having free end portions for fastening the absorbent article around the waist of a wearer and attachment end portions that are fixedly attached to the outside of the back-sheet or to the outside of the top-sheet, wherein the free end portions of the elongate belts overlap and the free end portions of the first elongate belt and the second elongate belt are fastened together by at least one breakable bond that is arranged in the overlap, wherein the first elongate belt and the second elongate belt overlap substantially only at the breakable bond;
 wherein the free end portions are arranged within the boundaries of the top-sheet and/or the back-sheet, and
 wherein the first elongate belt and the second elongate belt are fastened to each other at the free end portions before the article is used.

2. The absorbent article according to claim 1, wherein the free end portion of the first elongate belt is directed towards the attachment end portion of the second elongate belt.

3. The absorbent article according to claim 1, wherein each attachment end portion of the first and second elongate belts is longitudinally spaced apart from a corresponding free end portion of the first and second elongate belts.

4. The absorbent article according to claim 1, further comprising an absorbent core that is situated on the inner side of the back-sheet, the absorbent core being intended to be directed towards the wearer when the absorbent article is worn.

5. The absorbent article according to claim 1, wherein the breakable bond is re-fastenable.

6. The absorbent article according to claim 1, wherein at least one of the free end portions is attached to the back-sheet or to the top-sheet by a breakable bond.

7. The absorbent article according to claim 1, wherein at least one of the first and second elongate belts is folded in order to wrap up a length of the at least one of the first and second elongate belts.

8. The absorbent article according to claim 7, wherein at least one of the first and second elongate belts is folded in a Z-shape.

9. The absorbent article according to claim 1, wherein the longitudinal extension of at least one of the first and second elongate belts is equal to, or is longer than, the maximum lateral extension of the top-sheet and/or the back-sheet.

10. The absorbent article according to claim 5, wherein the breakable bond comprises a hook and loop arrangement, or an adhesive pad and a plastic film.

11. The absorbent article according to claim 1, wherein the free end portions of the elongate belts overlap each other before the article is used.

12. The absorbent article according to claim 1, wherein the absorbent article comprises a longitudinal dimension and a transverse dimension perpendicular to the longitudinal dimension, the longitudinal dimension being greater than the transverse dimension, and the first and second elongate belts extend in a direction parallel to the transverse dimension.

13. The absorbent article according to claim 1, wherein the absorbent article comprises a front portion, a crotch portion and a rear portion, and the free end portions and the attachment end portions of the first and second elongate belts are either all provided together with the overlap in the front portion or are all provided together with the overlap in the rear portion.

\* \* \* \* \*